US008673107B2

(12) United States Patent
Haushalter (10) Patent No.: US 8,673,107 B2
(45) Date of Patent: Mar. 18, 2014

(54) METHODS FOR FABRICATING OPTICALLY ENCODED PARTICLES AND METHODS FOR OPTICALLY ENCODING OBJECTS WITH SUCH PARTICLES

(75) Inventor: Robert C. Haushalter, Los Gatos, CA (US)

(73) Assignee: Parallel Synthesis Technologies, Santa Clara, CA (US)

( * ) Notice: Subject to any disclaimer, the term of this patent is extended or adjusted under 35 U.S.C. 154(b) by 0 days.

(21) Appl. No.: 12/091,900

(22) PCT Filed: Oct. 30, 2006

(86) PCT No.: PCT/US2006/042359
§ 371 (c)(1),
(2), (4) Date: Sep. 22, 2008

(87) PCT Pub. No.: WO2007/051035
PCT Pub. Date: May 3, 2007

(65) Prior Publication Data
US 2009/0218805 A1    Sep. 3, 2009

Related U.S. Application Data

(60) Provisional application No. 60/731,203, filed on Oct. 28, 2005.

(51) Int. Cl.
*C09J 5/10* (2006.01)
*B32B 37/14* (2006.01)
*B32B 38/10* (2006.01)

(52) U.S. Cl.
USPC ............... 156/306.6; 156/277; 156/308.4; 156/308.6; 705/62; 705/317; 705/318; 705/325

(58) Field of Classification Search
USPC ........... 156/277, 305.6, 308.4, 308.6; 705/62, 705/317, 318, 325
See application file for complete search history.

(56) References Cited

U.S. PATENT DOCUMENTS 3,412,245 A    11/1968    Halverson
3,473,027 A    10/1969    Freeman et al.
(Continued)

FOREIGN PATENT DOCUMENTS

EP    1491350 A2    12/2004
EP    1491350 A3    8/2005

OTHER PUBLICATIONS

Definition of "print"—Merriam-Webster Dictionary; Dec. 2011.*
(Continued)

*Primary Examiner* — Sonya Mazumdar
(74) *Attorney, Agent, or Firm* — Kaplan Breyer Schwarz & Ottesen, LLP (57) ABSTRACT

A method for labeling an object such as a biological sample, including printing at least two different light-emitting species onto a substrate which are capable of displaying a unique optical signature when excited; and externally attaching the object to the printed at least two different light-emitting species. Also, a method for conducting a large scale test, including printing a first label onto a first substrate, the first label comprising at least two different light-emitting species capable of displaying a first unique optical signature when excited; printing a second label onto the first substrate or a second substrate, the second label comprising at least two different light-emitting species capable of displaying a second unique optical signature when excited; externally attaching a first object, such as a first biological sample to the first label; externally attaching a second object, such as a second biological sample to the second label; processing the first and second objects in a combined manner; analyzing the processed first and second objects; and identifying the analyzed first and second objects using their respective first and second labels.

28 Claims, 5 Drawing Sheets

(56) References Cited

U.S. PATENT DOCUMENTS

| | | | |
|---|---|---|---|
| 4,018,635 | A | 4/1977 | Ryan et al. |
| 4,491,620 | A | 1/1985 | Joiner, Jr. |
| 4,816,344 | A | 3/1989 | Chiang |
| 5,043,265 | A | 8/1991 | Tanke et al. |
| 5,329,127 | A | 7/1994 | Becker et al. |
| 5,674,698 | A | 10/1997 | Zarling et al. |
| 5,698,397 | A | 12/1997 | Zarling et al. |
| 5,891,656 | A | 4/1999 | Zarling et al. |
| 6,159,686 | A | 12/2000 | Kardos et al. |
| 6,201,989 | B1 | 3/2001 | Whitehead et al. |
| 6,207,130 | B1 | 3/2001 | Kareiva et al. |
| 6,399,397 | B1 | 6/2002 | Zarling et al. |
| 6,403,947 | B1 | 6/2002 | Hoyt et al. |
| 6,514,295 | B1 | 2/2003 | Chandler et al. |
| 6,537,829 | B1 | 3/2003 | Zarling et al. |
| 6,552,290 | B1* | 4/2003 | Lawandy ............... 209/576 |
| 6,692,031 | B2* | 2/2004 | McGrew ................. 283/93 |
| 7,309,568 | B2* | 12/2007 | Oshida et al. ............ 435/6.11 |
| 2001/0049101 | A1 | 12/2001 | Brogger et al. |
| 2002/0022273 | A1 | 2/2002 | Empedocles et al. |
| 2002/0025490 | A1 | 2/2002 | Shchegolikhin et al. |
| 2002/0041372 | A1 | 4/2002 | Gardner et al. |
| 2003/0002029 | A1 | 1/2003 | Dukler et al. |
| 2003/0098357 | A1* | 5/2003 | Cummings et al. ......... 235/494 |
| 2003/0129296 | A1* | 7/2003 | Kelso ..................... 427/2.1 |
| 2003/0180482 | A1* | 9/2003 | Narita et al. ............. 428/32.6 |
| 2003/0207331 | A1 | 11/2003 | Wilson et al. |
| 2004/0072233 | A1 | 4/2004 | Kauvar et al. |
| 2004/0099740 | A1 | 5/2004 | Chresand et al. |
| 2004/0217298 | A1 | 11/2004 | Bawendi et al. |
| 2004/0217364 | A1 | 11/2004 | Tarsa et al. |
| 2005/0056183 | A1 | 3/2005 | Meshireri |
| 2005/0136486 | A1 | 6/2005 | Haushalter |
| 2005/0208543 | A1 | 9/2005 | Vann et al. |
| 2007/0011023 | A1* | 1/2007 | Silverbrook ................ 705/1 |
| 2009/0117340 | A1* | 5/2009 | Halfyard et al. ............ 428/195.1 |
| 2009/0159510 | A1 | 6/2009 | Haushalter |

OTHER PUBLICATIONS

W. H. Wright, et al., "Flow Cytometry with Upconverting Phosphors Reporters" in SPIE Proceedings: Optical Investigations of Cells in Vitro and In Vivo, D. L. Farkas, et al. (editors), vol. 3260, published Apr. 1998, pp. 245-254.

Officer, S., et al., "Novel online security system based on rare-earth-doped glass micro beads", Proceedings of the SPIE—The International Society for Optical Engineering, SPIE, USA, vol. 5310, No. 1, Jan. 20, 2004, pp. 387-395, XP002323046, ISSN 0277-786X.

Dejneka, M. J., et al., "Rare earth-doped glass microbeads", Proceedings of the National Academy of Sciences of USA, National Academy of Science, Washington, D.C., US vol. 100, No. 2, Jan. 21, 2003, pp. 389-393, XP002323047, ISSN 0027-8424.

Supplementary European Search Report for Application No. 05813069.1-1234/1812884 dated Aug. 5, 2009.

International Preliminary Report on Patentability for Application No. PCT/US2005/024174 filed Jul. 11, 2005.

International Published Application No. WO2006/017140 and International Search Report for Application No. PCT/US2005/024174 filed Jul. 11, 2005.

Written Opinion of the International Searching Authority for Application No. PCT/US2005/024174 filed Jul. 11, 2005.

International Preliminary Report on Patentability for Application No. PCT/US2005/038638 filed Oct. 24, 2005.

International Published Application No. WO2006/047621 and International Search Report for Application No. PCT/US2005/038638 filed Oct. 24, 2005.

Written Opinion of the International Searching Authority for Application No. PCT/US2005/038638 filed Oct. 24, 2005.

International Preliminary Report on Patentability for Application No. PCT/US2006/042359 filed Oct. 30, 2006.

International Published Application No. WO2007/051035 and International Search Report for Application No. PCT/US2006/042359 filed Oct. 30, 2006.

Written Opinion of the International Searching Authority for Application No. PCT/US2006/042359 filed Oct. 30, 2006.

Office Action dated Jul. 28, 2008 issued in co-pending U.S. Appl. No. 10/890,530, filed Jul. 12, 2004 of Robert C. Haushalter.

Office Action dated Mar. 13, 2009 issued in co-pending U.S. Appl. No. 10/890,530, filed Jul. 12, 2004 of Robert C. Haushalter.

Office Action dated Oct. 29, 2009 issued in co-pending U.S. Appl. No. 10/890,530, filed Jul. 12, 2004 of Robert C. Haushalter.

Office Action dated Jul. 21, 2010 issued in co-pending U.S. Appl. No. 10/890,530, filed Jul. 12, 2004 of Robert C. Haushalter.

"U.S. Appl. No. 10/890,530 Office Action", Mar. 30, 2011.

"U.S. Appl. No. 10/890,530 Office Action", Dec. 13, 2011.

"EP Application No. 05813069.1 Office Action", Oct. 5, 2011.

"U.S. Appl. No. 11/577,697 Office Action", Apr. 26, 2012.

* cited by examiner

METHODS FOR FABRICATING OPTICALLY ENCODED PARTICLES AND METHODS FOR OPTICALLY ENCODING OBJECTS WITH SUCH PARTICLES

RELATED APPLICATIONS

This application is a National Stage of International Application No. PCT/US2006/042359, filed on Oct. 30, 2006, published in English, which claims the benefit of U.S. Provisional Application Ser. No. 60/731,203, filed on Oct. 28, 2005. The contents of PCT/US2006/042359 and U.S. Provisional Application No. 60/731,203 are incorporated herein by reference.

FIELD OF THE INVENTION

The present invention relates to optical encoding. More specifically, the present invention relates to methods for fabricating optically encoded particles and methods for optically encoding objects with such particles.

BACKGROUND OF THE INVENTION

A large number of unique optical codes can be created with a class of rare earth based phosphor materials known as the PARALLUME™ materials as described below; These PARALLUME materials, which emit visible light upon excitation with either ultraviolet (UV) or infra red (IR) radiation, are excited at a single wavelength and subsequently emit several different colors of light into very narrow bands from several different rare earth emitting centers. A PARALLUME material contains one or more light-emitting species. The relative integrated emission intensities of two (2) or more light-emitting species (supplied by one or more PARALLUME materials) can be measured and represent an optical code as shown in FIGS. 1a-d. The UV→VIS process is referred to as a downconversion process as the higher energy UV is converted to lower energy visible light. The multicolor emitter materials that undergo this process are called the PARALLUME-UV materials. Another class of rare earth phosphors that contain ytterbium can convert near IR radiation into multicolored visible light by means of a multiphoton upconversion process and these materials are known as the PARALLUME-IR materials.

An optical barcode or unique optical signature can be generated using the PARALLUME materials by measuring the ratio of two different emitting species. The relative integrated emission intensities of two or more emitters within each PARALLUME composition can represent an optical barcode. For example, if a PARALLUME material contained two emitters, such as A and B, then a certain number of optical codes based on the relative emitting ratios of the two emitters can be resolved. If A and B could be optically resolved at 10% compositional intervals, then ten different compositions exist each of which represent a different ratio of the two emitters and therefore the system is said to have a multiplexing level of 10. The method by which the optical code is generated is by integrating the relative intensity of the emission peaks.

Figure 1:
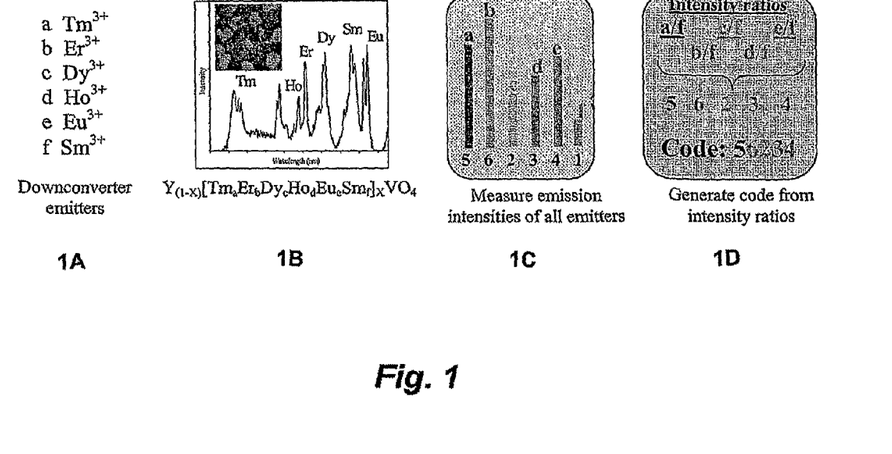
Figure 2:
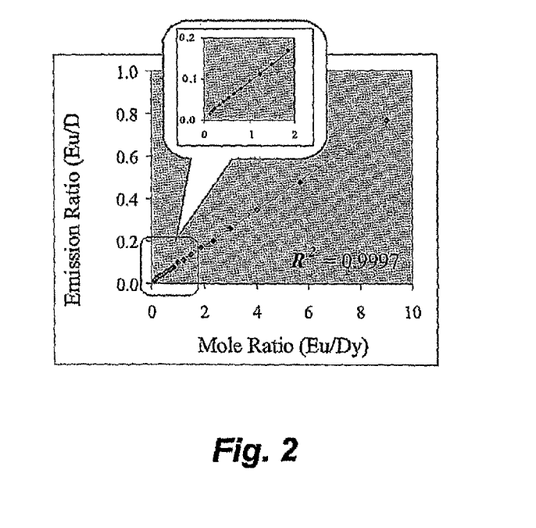
FIG. 2 is a graph illustrating a decoding or calibration plot which shows the linear relationship between emission ratio and mole ratio of a binary phase spread library (Eu and Dy) of samples ranging from 10% to 90% with 5% increment levels.

In practice, the code is always generated by analyzing the emission peak intensities in pairs of peaks to generate a ratio. For example, FIG. 2 shows a plot of the number of atoms of two emitters versus the ratio of the emission peak intensity from the two emitters.

There are two methods of synthesizing the PARALLUME materials so that two or more emitters are available to create the ratiometric based optical code. The two methods are to: (a) mix two or more emitters together to generate a known ratio by, for example, weighing various amounts of the two components or (b) synthesizing a single host material that contains known amounts of two or more emitters within the same crystallographic lattice. For the PARALLUME-UV downconverting compositions more precise definitions can be given for these two cases (a) and (b) directly above as:

(1) A downconverting composition comprising two or more lanthanide materials, wherein each lanthanide material comprises a host, an absorber, which can be the host itself, and one or more emitters, and wherein the materials emit detectable electromagnetic radiation upon excitation with absorbable electromagnetic energy, and wherein the emitted radiation is of a longer wavelength, or lower energy, than the absorbed radiation, and wherein one or more relative ratios of emission intensities uniquely identify the composition.

(2) A downconverting composition comprising a lanthanide material, wherein the lanthanide material comprises a host, an absorber which can be the host itself, and two or more emitters, and wherein the material emits detectable electromagnetic radiation upon excitation with absorbable electromagnetic energy, and wherein the emitted radiation is of a longer wavelength, or lower energy, than the absorbed radiation, and wherein one or more relative ratios of emission intensities uniquely identify the composition.

For the PARALLUME-IR materials, the compositions required to create ratios from the measurement of the integrated emission intensities of more than one emitter can be similarly prepared.

Because of the very narrow emission peak width of the rare earth centers in the PARALLUME materials, it is possible to measure the relative integrated intensity of the emission peaks with a very high degree of accuracy typically less than a percent coefficient of variance (% CV=standard deviation/ mean×100) of less than 0.2-3%. Thus the multicolor emitting PARALLUME materials are capable of labeling and uniquely identifying millions of samples.

Many problems arise when developing a process to measure larger and larger numbers of samples but two of the more outstanding of these problems are (a) difficulties in labeling sufficiently large number of samples (insufficient multiplexing depth) because of the inability of the optical encoding system to generate a sufficient number of unique resolvable signatures and, (b) even if a method exists in principle to label and distinguish very large numbers of samples difficulties are often encountered in the logistics of actually synthesizing more than hundreds of samples.

An extremely high level of optical multiplexing has been previously demonstrated in the patent pending PARALLUME-UV and PARALLUME-IR materials with up to hundreds of thousands of optical codes in the PARALLUME-IR materials and billions of codes in the PARALLUME-UV materials statistically demonstrated. Since both of the commercially available optically encoded bead sets, such as those from Luminex and Quantum Dot (QD) Corporation, only have a multiplexing level of 100, this means that only 100 samples can be distinguished with a unique set of optical signatures before "running out" of unique codes. The current 100 level multiplexing limit is primarily due to the inherently broader emission peak widths in the organics dyes and quantum dots used to create the Luminex and QD optical codes and the fact that each dye or quantum dot has its own different excitation spectrum requiring multiple excitation sources for maximum brightness. The wider the emission peaks the fewer peaks can be resolved within a given wavelength range. While the relative integrated intensity of non-overlapping peaks can be obtained easily and accurately, as soon as emission peaks in a spectrum begin to display appreciable overlap the ability to integrate relative intensity is severely degraded. Since the PARALLUME optical codes are based on rare earth emitters, which have an inherently narrower peak width than the organic dyes or QDs, the PARALLUME materials can support a much deeper level of multiplexing.

Because the Luminex and QD systems have such a low level of multiplexing, practitioners of these technologies have never been faced with the daunting task of synthesizing tens or hundreds of thousands, or even millions, of different compounds. But in order to satisfy the synthetic requirements of a very deeply multiplexed system such as the PARALLUME-IR and PARALLUME-UV, the serially executed synthesis used for dozens of samples is totally inadequate and a new method is required. Currently for example, one common way to prepare encoded beads is to entrain particles much finer than the final desired bead size within a polystyrene particle. The common magnetic beads are prepared by polymerizing styrene in the presence of appropriately sized particles of magnetite. But such serial methods would be totally inadequate for the numbers of samples required for large scale gene expression or genotyping experiments or for any sort of attribution or anticounterfeiting applications.

Therefore, when devising such a method for the fabrication of very large numbers of encoded beads or particles, the following requirements and attributes should be considered:

Synthesis Speed An examination of the number of syntheses required with respect to the time per synthesis (Table 1) shows that a very rapid synthesis method will be required. It is clear that normal serial synthesis methods will be totally inadequate to address the needs for highly parallel synthesis and that a new fabrication protocol is required.

TABLE 1

Samples prepared within a given time interval at a given synthesis rate

| Sample synthesis rate | Samples/day | Samples/year |
|---|---|---|
| One/hour | 10 | 2000 |
| One/minute | 500 | 100,000 |
| One/second | 30,000 | 6,000,000 |

Accuracy of Synthesis Since the optical code is based on the ratios of the relative integrated intensities of the emission peaks of the various emitters present, and intensity of the emitted peaks is proportional to the amount of emitting material present, it is clear that the accuracy of constructing the requisite ratios must be carried out with an accuracy at least greater than the resolution interval to be determined. Since the particles to be labeled are generally in the range of 1 to 100 microns, the fabrication methodology must prepare ratios of the constituent PARALLUME materials very accurately using extremely small amounts of materials.

Reproducibility of Synthesis The reproducibility of the synthetic procedure must be appreciably better than the resolution interval to be determined when constructing the optical code. As with the accuracy of the synthesis discussed above the reproducibility must conform to the requirement that only miniscule amounts of PARALLUME material are present in each particle or bead.

Format Flexibility The optically encoded particles will more useful if the method used to fabricate the particles has the maximum flexibility in terms of such parameters as:

Number of particles Ideally the total number of particles, as well as the number of replicate particles, required for a given application could be controlled and be related to the number of variables or samples to be investigated. No extra particles need be prepared and all of the particles prepared would be used.

Particle Size The particle size must be compatible with the object to be labeled or identified. There are uses for labels in all size ranges. Larger labels can be prepared for compositions that are more difficult to read due to lack of brightness.

Particle Composition It would be desirable to have total compositional flexibility. By controlling the composition one can exactly match the optical multiplexing depth to the number of samples to be measured thereby spreading the code over the maximum compositional spread range and generating the easiest to read code.

There are two primary means by which particles are currently optically encoded depending on what the emitting species within the particles is. The two types are the organic dye molecule emitters, such as those found in the Luminex™ type products, and the quantum dot emitters from Quantum Dot Corporation™. The organic dye molecules are generally formed as a monomer with an appropriate functionality which becomes incorporated into a polymerizing system such as polystyrene during the formation of polystyrene beads. The quantum dot materials are either used directly or attached to other molecules or solids via an appropriate functional group. Alternatively, QD particles can be entrained in a system that is undergoing polymerization. For example, if a system consisting of small, monodisperse polystyrene beads is subjected to polymerization with, for example, styrene in the presence of the small QD particles (the QD particles are generally smaller than 10 nm in size), the small polystyrene bead will act as a site for the polymerization and the QD particles will be entrained in the polymerizing styrene. Thus the QD particles are trapped within the growing polystyrene bead. It should be noted that one of the primary difficulties with using either of these technologies is that both only provide for a 100 member bead set as of the time of this writing (2005). Therefore only 100 objects can be labeled and differentiated from one another in an experiment greatly limiting their utility as labels for sample numbers large enough to satisfy the requirements of high throughput experimentation.

A problem with both of these synthetic approaches is that the fabrication methods are incapable of producing millions of different codes within a very short period of time, e.g. less than 24 hours/million samples.

Accordingly, a method is needed for fabricating millions of different codes within a very short period of time and for encoding objects with such codes within such time periods.

SUMMARY

In one embodiment, a method for labeling an object, comprising printing at least two different light-emitting species onto a substrate which are capable of displaying a unique optical signature when excited; and externally attaching the object to the printed at least two different light-emitting species.

In another embodiment, a method for conducting a large scale test, comprising printing a first label onto a first substrate, the first label comprising at least two different light-emitting species capable of displaying a first unique optical signature when excited; printing a second label onto the first substrate or a second substrate, the second label comprising at least two different light-emitting species capable of displaying a second unique optical signature when excited; externally attaching a first object to the first label; externally attaching a second object to the second label; processing the first and second objects in a combined manner; analyzing the processed first and second objects; and identifying the analyzed first and second objects using their respective first and second labels.

In a further embodiment, a label for an object, comprising: at least one printed particle including at least two different light-emitting species capable of displaying a unique optical signature when excited.

BRIEF DESCRIPTION OF THE DRAWINGS

FIGS. 1a-d illustrate an exemplary method for generating an optical signature or "barcode" from light emitted by a rare earth downconverting phosphor composition of the invention, which has been combined with an object. FIG. 1a depicts downconverter emitters. FIG. 1b is a graph illustrating a spectrum generated by the composition combined with the object, after excitation with energy of a predetermined wavelength. FIG. 1c is a graph showing measurements of the relative integrated intensity of the various colors of light emitted by the composition combined with the object. FIG. 1d is a graph showing the optical barcode generated from ratios of the intensities of the various colors of light emitted by the composition combined with the object.

FIGS. 4a-d schematically depict an embodiment of a method for fabricating optically encoded particles using thermal wax transfer printing methods.

FIG. 7a-h schematically depict an embodiment of a method for using optically encoded particles to perform a large scale biological experiment.

DETAILED DESCRIPTION

Described herein is a method for fabricating optically encoded particles wherein each individual particle is capable of, when appropriately excited, displaying its own unique optical signature arising from the emitted intensity ratios of several different light emitting species. The method generally comprises printing two or more rare earth emitting species, on a substrate using, for example, any commercially available printing apparatus or printing technique capable of precisely mixing two or more components, i.e. different colored inks, waxes or toners, in an extremely precise manner, and printing the components on the substrate in a very small area and in very fast and highly reproducible manner. Fabricating the optically encoded particles by printing allows the particles to be made at a very rapid rate, e.g., up to a million encoded particles may be fabricated within a day or less.

It should be understood that the optically encoded particle fabrication method described herein is not intended to be limited to the printing devices and printing methods described herein and that other suitable types of printing devices and printing methods may be used for fabricating the optically encoded particles.

In one illustrative embodiment of the method, a set of six different types of optically encoded particles are printed on different regions of a substrate from a mixture of two different emitter materials A and B (e.g. fluorescent dyes or phosphors), i.e. $A_{1-x}B_x$, with x=0.2, 0.4, 0.6 and 0.8, wherein each particle in each region contains the appropriate amounts of A and B to produce the desired ratios. The particles are differentiated from each other (identified) by appropriately exciting the particles such that the emitters A and B release radiation at two different wavelengths. Since the amount of light emitted by A and B is proportional to the amount of A and B present in the particle if there is no optical interaction between A and B, each printed region can be identified by the ratio of the observed integrated intensity of the two emitters. The number of resolvable particles is often referred to as the degree or depth of multiplexing.

In embodiments where the optically encoded particles are to be printed starting from n different colored "ink" sources, the required ratio may be printed onto the desired region to be encoded by either (a) printing thin layers of the various single emitters on top of one another or (b) printing various single emitters as a series of closely spaced dots where the ratios of the various emitters are determined by the area, thickness and areal density of the various spots dithered together to render the desired emitter ratios within the area to be integrated. The printing methods that may be used for printing the particles include, without limitation, ink jet printing, thermal wax transfer printing, contact printing or any other suitable printing method capable of printing layers, films, or dots of very carefully controlled and arbitrary composition, at very high production rates and preferably, at very low costs. The printing technique should allow the production of any desired particle composition at rates of up to millions per hour.

Although the above described embodiment involved printing from multiple ink sources, one of ordinary skill in the art will appreciate that particles optically encoded with a single code may also be fabricated by printing method using a single ink source.

Figure 3:
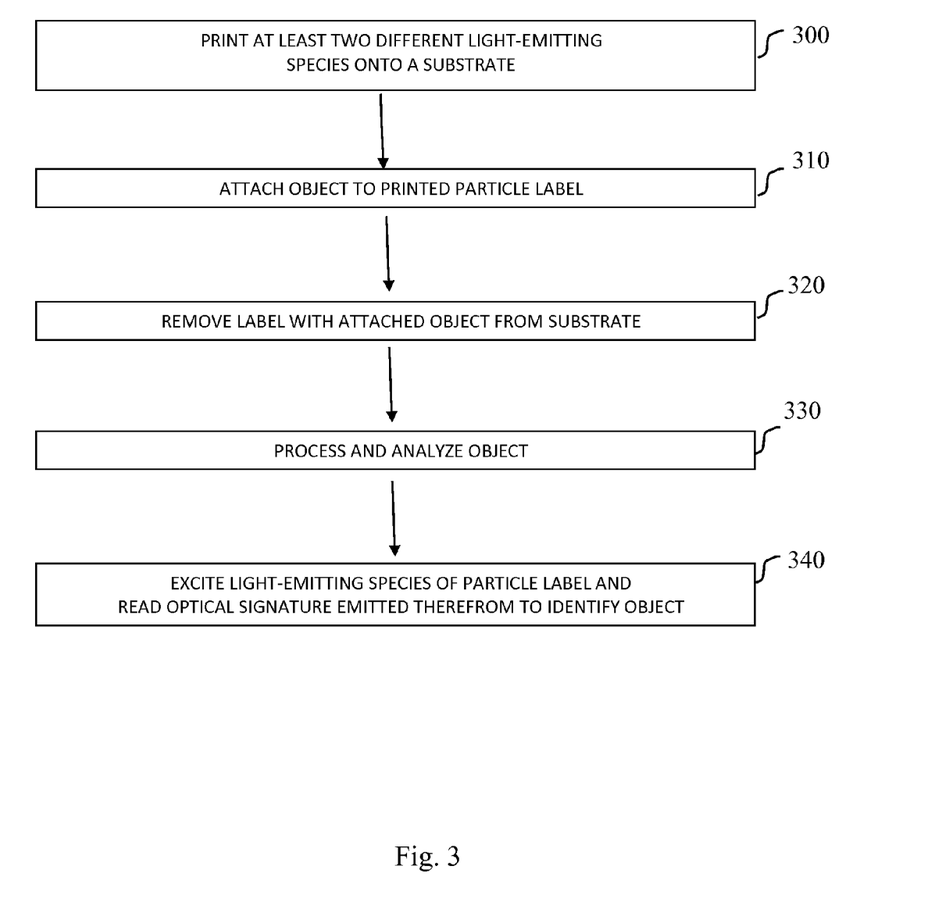
FIG. 3 is a flowchart illustrating an embodiment of the method as applied to the preparation of objects, e.g., biological samples, for high throughput testing and screening.

The encoded particle fabrication method may be used in the preparation of biological samples for high throughput testing and screening. FIG. 3 is a flowchart illustrating ah embodiment of the method as applied to the preparation of biological samples for high throughput testing and screening. In step 300, a thermal wax transfer printer capable of printing thousands of 100 micron regions, is used for printing a label onto a substrate, the label formed by one or more particles and comprising at least two different light-emitting species capable of displaying a unique optical signature when appropriately excited. In some embodiments, the at least two different light-emitting species are provided by a single PARALLUME material. In some embodiments, the at least two different light-emitting species are provided by at least two PARALLUME materials. In other embodiments, the PARALLUME materials) may be combined with one or more other materials each having one or more light-emitting species. For a more detailed description of PARALLUME materials, see U.S. patent application Ser. No. 10/890,530, filed Jul. 12, 2004 entitled Methods For Optically Encoding An Object With Upconverting Materials And Compositions Used Therein, and International Application Serial No. PCT/US05/38638, filed Oct. 24, 2005 entitled Rare Earth Downconverting Phosphor Compositions For Optically Encoding Objects And Methods And Apparatus Relating To Same, both of which are incorporated herein by reference. The substrate, in one illustrative embodiment, may comprise a polyester sheet coated with a film of a water soluble release agent. The light-emitting species or materials used by the thermal wax transfer printer may, in one illustrative embodiment, comprise thermal wax transfer ribbons containing doped samples of $YVO_4$, which contain various amounts of $Dy^{3+}$, $Er^{3+}$, $Eu^{3+}$, $Ho^{3+}$, $Sm^{3+}$ and $Tm^{3+}$, that emit visible radiation into many narrow bands when excited with ultraviolet radiation such as the 325 nm line of a He—Cd laser. As will be explained further on, the ratios of the integrated intensities of the six emitters will be measured and used to uniquely identify each printed particle.

After the encoded particles (typically thousands of particles) are printed on the substrate, in step 310, objects, e.g., samples of a biological material such as DNA, are attached to the outer surface(s) of the optically encoded particle. The samples of biological material may be attached to the particles using microcontact printing, ink jet printing or any other suitable printing or dispensing apparatus or method.

The printed particles may be used directly on the substrate onto which they were printed or if desired, in step 320 processed to be free floating in order to move, dispense or analyze the particles. The latter can be accomplished in one embodiment by printing onto a substrate which has poor adhesion for the particles or onto a layer that can be subsequently removed such as, for example, printing onto a water soluble release layer which will allow the particles to be washed off of the printing substrate. In alternate embodiments, free floating particles can be provided by using a printing method such as ink-jet printing, wherein the ejected material can be evaporated, precipitated or solidified by ejecting the droplets into a gas or liquid where they can be collected.

In step 330, the objects, whether on the substrate or free floating, are parallel processed and analyzed.

In step 340, each object with its attached optically encoded particle or particles, is identified by appropriately exciting and then reading (decoding) the optical signature of its corresponding attached particle(s). Hence, the optically encoded particle(s) act as a label or optical barcode to identify the corresponding object. The encoded particles may be excited using any suitable excitation method. For example, in some embodiments, ultraviolet, infrared, x-ray, or microwave electromagnetic radiation may be used for exciting the encoded particles. In other embodiments, excitation may be performed using electroluminescence, piezoelectric, pyroelectric, thermal, or magnetic excitation methods, to name a few.

The use of the encoded particle fabrication method in the preparation of biological samples for high throughput testing and screening, provides synthesis speed. If a single bead set can contain millions of distinguishable members then to take full advantage of that bead set's full multiplexing ability one has to prepare the samples at a very fast rate in order to prepare the full bead set within a reasonable amount of time, i.e. minutes or hours. Table 2 shows the number of particles per 50,000 mm², which is approximately the printable area of a typical sheet of paper (8.5 inches×11 inches), that can be printed for a given particle size with the particles covering either 50% or 100% of the printable surface of the sheet of paper.

TABLE 2

| Number of Particles per 50,000 mm² Printable Substrate Area | | | |
|---|---|---|---|
| Size of particle (μm²) | Particle spacing (μ) | Substrate coverage: particle + space (μ²) | Number of squares |
| 100 × 100 | 200 (50% cover) | 200 × 200 | 1,250,000 |
|  | 100 (100% cover) | 100 × 100 | 5,000,000 |
| 25 × 25 | 50 (50% cover) | 50 × 50 | 20,000,000 |
|  | 25 (100% cover) | 25 × 25 | 80,000,000 |
| 10 × 10 | 20 (50% cover) | 20 × 20 | 125,000,000 |
|  | 10 (100% cover) | 10 × 10 | 500,000,000 |

In one embodiment, a 2540 dpi printer is capable of printing one pixel having a size of about 10 μm. Accordingly, such a printer is capable of printing about 484,000,000 pixels or particles on a sheet of 8.5×11 paper. If one sheet at 100% coverage can be printed in 20 minutes, then the particle fabrication method is capable of producing about 24,000,000 particles per minute. If the printer speed is increased to 5 minutes/page, then the particle production rate may be as high as 100,000,000 particles per minute.

The printing method also provides accurate and reproducible particles because color printers are capable of reproducing the millions of requisite colors from conventional computer programs. This means that printers are capable of mixing exactly the right amount of three or four different dyes or pigments in an extremely precise and reproducible manner otherwise printed images would look different each time they were printed.

The printing method offers a number of important benefits for the preparation of optically encoded particles. These include, without limitation, flexibility in particle attributes such as the number, type, size, volume, number of colors, number of particles per unit area of printing substrates, range of optical encoding materials present relative to one another within a given particle and type of substrate on which the encoded particles may be printed.

Number of particles As discussed above very large numbers of particles can be produced per unit time. Printing technology can produce the desired number of particles needed for a given effort without producing excess unheeded particles.

Particle Size A printer can make a continuous sample from a single pixel to covering an entire sheet so there is total flexibility in particle size between these two extremes.

Particle Composition Since the printer can very precisely dispense and control the relative amounts of the various colored "inks", the printer provides a very convenient means of very accurately assembling precise amounts of different materials within a very small dimensional area. This means that in the case of using the printer to create optically encoded materials any given code (i.e. any given arbitrary ratios of emitters) based on the ratios of various emitters can be prepared.

The following discussion describes a few illustrative examples of optically encoded particles fabricated by printing with PARALLUME or other materials, and uses for such particles.

Example 1

Fabrication of Optically Encoded Particles Using Thermal Wax Transfer Printing Technology In this example, optically encoded particles may be printed on a substrate using thermal wax transfer (TWT) printing equipment. TWT printing is used for many of the most demanding printing applications where environmental stability and inertness are of paramount importance. Examples of items that can be printed on include machinery and equipment that sit outdoors, wood at a lumber yard and plants at a nursery. TWT printers with very high resolution are commercially available from a number of sources and the printer and media costs are not largely different than high end ink jet printing.

Figure 4:
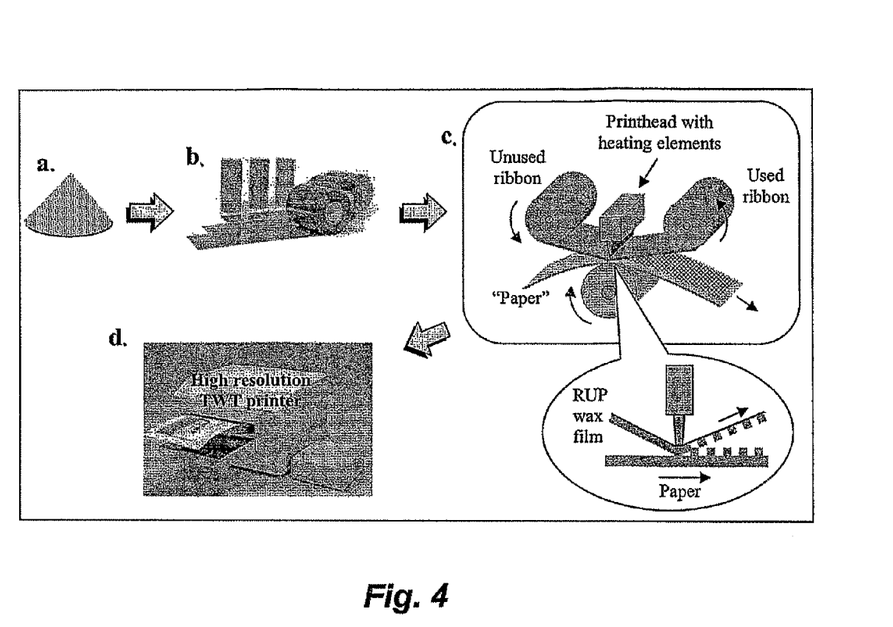

TWT printing uses rolls of "wax" which comprise complex mixtures of various organic resins and polymers, fillers and pigments. The resin, which is formulated as a melt or dissolved in organic solvents, may incorporate large amounts of solids without separation or degradation in printing performance even at amounts of over 50% by volume. As schematically depicted in FIG. 4a-d, TWT printing media (ribbons FIG. 4b) containing PARALLUME may be made using conventional methods, as TWT printing media already include silicon and titania fillers. Thus PARALLUME powders; (FIG. 4a) can be easily incorporated into conventional TWT formulations. The printing ribbon (containing one of more of the PARALLUME materials) is positioned under a printhead that contains extremely small heating elements as depicted in FIGS. 4c and 4d. As the ribbon is positioned under the printhead contact is made from the side opposite the substrate to be printed with a heating element. The printhead heating element melts a very small region of the wax on the ribbon which, when pressed against the substrate, adheres as the head is withdrawn leaving a particle (pixel) of resin on the substrate. Although TWT printing technology may be used to print onto any substrate, the higher resolution images may be achieved by printing onto polyester or other polymer sheet films.

Figure 5:
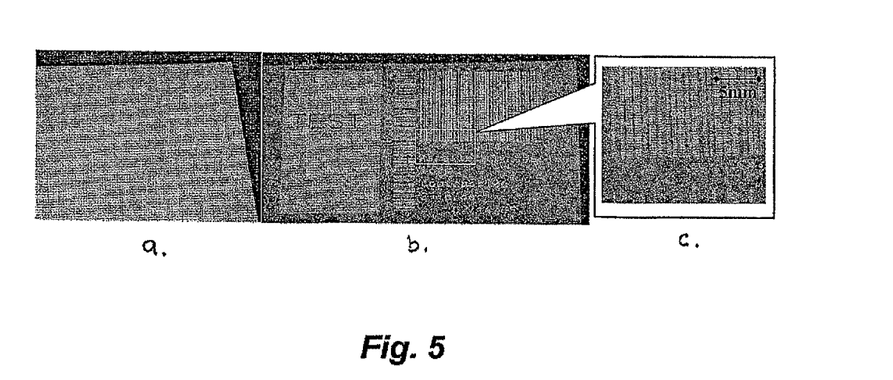
FIGS. 5a-c show a polyester sheet printed with a PARALLUME-UV containing thermal wax transfer ink under visible illumination (FIG. 5a) and under UV illumination (FIGS. 5b and 5c).

A sample of an encoded substrate printed using TWT technology, which only contains a single ratio (i.e. two light-emitters). FIG. 5a shows a polyester sheet printed with a PARALLUME-UV (Dy:Eu 1:1) containing thermal wax transfer ink under visible illumination and FIGS. 5b and 5c show the same printed polyester sheet under UV illumination. The percentage of CV on intensity ratio variation of a uniform area on the printed sheet is about 1.8%. Excellent resolution can be observed in FIG. 5c.

Example 2

Using the Encoded Particles to Label Biological Samples

In order to identify and track a set of biological molecules, the biological molecules must be attached to the outer surface of the encoded particles. Recall that the PARALLUME optical encoding technology serves the same function as that of an x,y address on a chip based assay, i.e. that of an identifying label and not as a "reporter" entity which provides information about the assay or chemistry that is occurring in the system. The encoded particle is designed to be used as a label to identify an object to which it is attached or molecules attached to it but not to interfere with any pre-existing color based assay or procedures. The non-interference aspect can be accomplished either by (a) choosing a barcode-reporter combination where there are separate excitation sources that can each excite either the reporter and barcode but not the other and (b) resolving the emission in time as in the case of differentiating prompt emission from organic dyes or quantum dots from the slower emission from lanthanide based materials.

Figure 6:
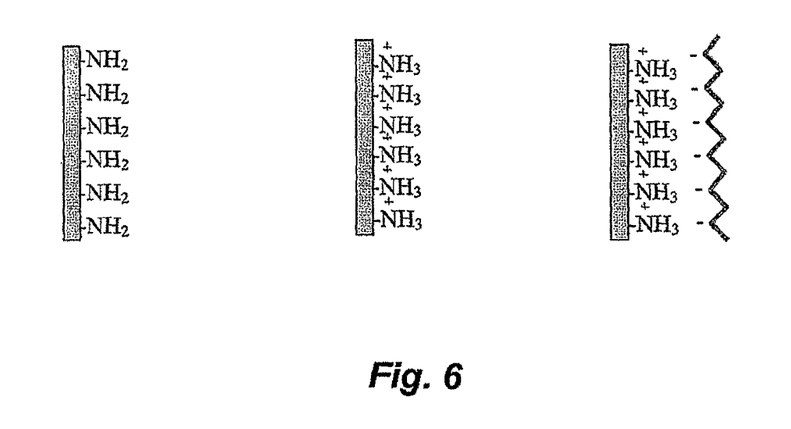
FIG. 6 graphically illustrates that the incorporation of alkylamino substituted polystyrene into the thermal wax transfer printing ink formulation provides pendant surface amino groups and that at neutral pH, these amino groups are protonated and will strongly bind the DNA.
Figure 7:
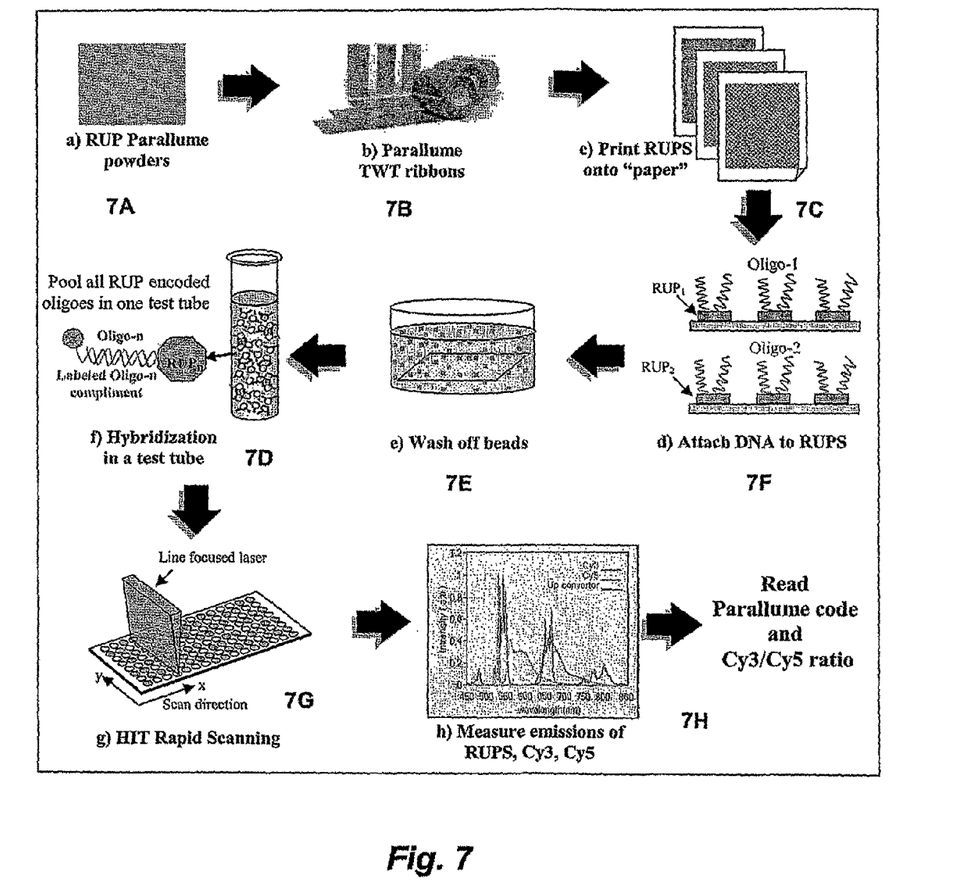

There are several ways in which to attach the printed particle(s). In a preferred embodiment, polymers are incorporated with the appropriate functional groups into the TWT polymer resin formulation. In another embodiment, microcontact printing can be used to attach the object to be identified to the particle(s), which is similar to the method by which DNA is bound to the glass slide when fabricating DNA microarrays by microcontact printing. On glass, the terminal amino group on a surface bound alkylamino group is protonated at pH7 and the resulting polycationic ammonium surface strongly binds the polyanionic DNA in a strong ionic fashion as shown in FIG. 6.

This may be accomplished in the case of the printable PARALLUME encoded particles by the addition of an alkylamino functionalized polystyrene polymer into the TWT resin formulation, which may also beneficially improve the wetting properties of the particles. Since it is well known that the commercially available polystyrene beads that are functionalized with alkylamino groups can function in a similar capacity as the amino groups on a glass surface, TWT formulations containing a sufficient number of accessible amino groups would function similarly.

It should be understood, that many other organic functional groups, or inorganic materials, other than those mentioned, herein may also be incorporated into or made a part of the printing formulation.

In another embodiment, DNA may be attached to encoded particles with amino functionalized surfaces by using one of several known methods for covalently attaching an oligonucleotide to amino groups. Most of these are based on functionalizing the terminal ribose —OH group to provide an amino group. The N-functionalized oligonucleotide is then reacted with the amino surface of the encoded particle, which was previously treated with an excess of a cross linking reagent such as glutaraldehyde, to form a stable covalent amide linkage. Even more convenient for this purpose, but expensive, are the bis-phosphoramidite linkers available from Glen Research.

In still another embodiment, very finely divided silica may be added to the encoded particle resin formulation, etching the surface free of resin (with, for example, an oxygen plasma or UV/ozone treatment) to expose the embedded silica and then functionalizing the silica exposed silica as per glass microarray slides.

Those skilled in the art will appreciate that there are many other methods that may be used for attaching DNA, RNA, proteins or other molecules to the encoded particles by incorporating a suitably reactive functionality in the ink formulation.

Example 3

Preparation and Use of Optically Encoded Particles Using Ink Jet Printing Technology Optically encoded particles may be fabricated using materials similar to those described above in Example 1 using an inkjet printer instead of the TWT printer. In order to prepare the ink formulation, the PARALLUME materials are prepared in a very finely divided state. The materials can be either chemically synthesized in the form of colloids or prepared by a technique such as flame spray pyrolysis that gives very small particles with good crystallinity.

Example 4

Use of Encoded Particles To Perform a Large Scale Biological Experiment: Parallel Hybridization in Gene Expression Experiments The printed optically encoded particles can be used to perform large scale genotyping of gene expression experiments. The process using PARALLUME encoded particles to perform a massive, parallel gene expression experiment is schematically depicted in FIG. 7a-h. The optically encoded particles may be formulated using TWT printing methods described in Example 1 above. Specifically, four (4) Parallume powders in FIG. 7a, each with an Er, Ho, Tm and Pr light-emitter, are fabricated into TWT ribbons in FIG. 7b. The TWT ribbons are used to print arrays of optically encoded particles of any type, size, or format each with any desired ratio of the four colors onto polyester film "paper" substrates in FIG. 7c. The substrate onto which the encoded particles are printed is treated with a release agent that will allow the subsequent removal of the particles from the substrate in order to process and analyze them in parallel. Next, using an inkjet or microcontact printer, the same or different oligonucleotides are attached to each known optical particle, in any desired format in FIG. 7d. The particles are then washed from the substrates in FIG. 7e and then subjected to a pooled, parallel hybridization reaction in FIG. 7f, using a common cy3/cy5 dye labeling scheme for sample and control target DNA. The particles may be hybridized in parallel millions or billions at a time against the target DNA in a flask. The particles are then placed onto a substrate and analyzed using any suitable parallel scanning technique such as hyperspectral imaging (HIT) in FIG. 7g. The HIT rapidly acquires emission spectra of the RUP (rare earth upconverting phosphor) encoded particle with a 980 nm source and the cy3/cy5 emission ratio with 532 nm and 632 nm lasers. The oligonucleotide sample is identified from the RUP label or "barcode" and assigned to the measured cy3/cy5 ratio (h), which identifies the relative level of gene expression, according to conventional established procedures.

Example 5

Combinations with Other Emitting Species to Further Expand the Codes

Other emitting species, such as other phosphors dyes and pigments, may be added to the PARALLUME materials to further increase the number of optical codes that can be generated. In one embodiment, the presence or absence of a dye can double the number of encoded sample that may be resolved.

It should be understood that other suitable types of printers, printing fluids or printing media, substrates and printing methods may be used for fabricating and using optically encoded particles described herein.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A method for labeling an object, the method comprising the steps of:
    printing a particle label onto a substrate, the particle label comprising at least first and second different light-emitting species having a molar ratio, the first light-emitting species emitting a first emission of radiation of a first wavelength in response to excitation electromagnetic radiation of a first wavelength, the second light-emitting species emitting a second emission of radiation of a second wavelength in response to the excitation electromagnetic radiation of the first wavelength, wherein an internal relative emission intensity ratio obtained from the first emission of the first light-emitting species and the second emission of the second light-emitting species is substantially linearly related to the molar ratio of the first and second light emitting species; and
    attaching the object to the particle label, wherein the internal relative emission intensity ratio of the first emission of the first light-emitting species and second emission of the second light-emitting species, produces a unique optical signature that identifies the object.

2. The method of claim 1, wherein each of the at least first and second different light-emitting species is provided in an ink.

3. The method of claim 2, wherein the step of printing the particle label is performed by printing a first thin layer of material comprising one of the at least first and second different light-emitting species on the substrate and then printing a second thin layer of material comprising the other one of the at least first and second different light-emitting species over the first thin layer of material.

4. The method of claim 2, wherein the step of printing the particle label is performed by printing a first thin layer of material comprising one of the at least first and second different light-emitting species on the substrate and then printing a second thin layer of material comprising the other one of the at least first and second different light-emitting species on the substrate adjacent to the first thin layer.

5. The method of claim 4, wherein the step of attaching the object is performed by attaching the object across outer surfaces of the first and second thin layers.

6. The method of claim 1, wherein the at least first and second different light-emitting species are provided in a ribbon of wax.

7. The method of claim 6, wherein the step of printing the particle label is performed by melting a section of the ribbon of wax onto the substrate.

8. The method of claim 1, wherein at least one of the at least first and second different light-emitting species comprises a rare earth phosphor material.

9. A method for conducting a large scale test, the method comprising the steps of:
    printing a first label onto a first substrate, the first label comprising at least first and second different light-emitting species having a molar ratio, the first light-emitting species of the first label emitting a first emission of radiation of a first wavelength in response to excitation electromagnetic radiation of a first wavelength, the second light-emitting species of the first label emitting a second emission of radiation of a second wavelength in response to the excitation electromagnetic radiation of the first wavelength, wherein an internal relative emission intensity ratio obtained from the first emission of the first light-emitting species of the first label and the second emission of the second light-emitting species of the first label is substantially linearly related to the molar ratio of the first and second light emitting species of the first label;
    printing a second label onto the first substrate or a second substrate, the second label comprising at least first and second different light-emitting species having a molar ratio, the first light-emitting species of the second label emitting a first emission of radiation of a first wavelength in response to excitation electromagnetic radiation of a first wavelength, the second light-emitting species of the second label emitting a second emission of radiation of a second wavelength in response to the excitation electromagnetic radiation of the first wavelength, wherein an internal relative emission intensity ratio obtained from the first emission of the first light-emitting species of the second label and the second emission of the second light-emitting species of the second label is substantially linearly related to the molar ratio of the first and second light emitting species of the second label;

attaching a first object to the first label, wherein the internal relative emission intensity ratio of the first emission of the first light-emitting species of the first label and second emission of the second light-emitting species of the first label, produces a unique optical signature that identifies the first object;

attaching a second object to the second label, wherein the internal relative emission intensity ratio of the first emission of the first light-emitting species of the second label and second emission of the second light-emitting species of the second label, produces a unique optical signature that identifies the second object;

processing the first and second objects in a combined manner;

analyzing the processed first and second objects; and identifying the analyzed first and second objects using their respective first and second labels.

10. The method of claim 9, wherein each of the at least first and second different light-emitting species of at least one of the first and second labels is provided in an ink.

11. The method of claim 10, wherein at least one of the step of printing the first label and the step of printing the second label is performed by printing a first thin layer of material comprising one of the at least first and second different light-emitting species on the first or second substrate and then printing a second thin layer of material comprising the other one of the at least first and second different light-emitting species over the first thin layer.

12. The method of claim 10, wherein at least one of the step of printing the first label and the step of printing the second label is performed by printing a first thin layer of material comprising one of the at least first and second different light-emitting species on the first or second substrate and then printing a second thin layer of material comprising the other one of the at least first and second different light-emitting species on the first or second substrate adjacent to the first thin layer.

13. The method of claim 12, wherein at least one of the steps of attaching the first and second objects is performed by attaching the first or second objects across outer surfaces of the first and second thin layers.

14. The method of claim 9, wherein the at least first and second different light-emitting species of at least one of the first and second labels are provided in a ribbon of wax.

15. The method of claim 14, wherein at least one of the step of printing the first label and the step of printing the second label is performed by melting a section of the ribbon of wax onto the substrate.

16. The method of claim 9, wherein at least one of the at least first and second different light-emitting species comprises a rare earth phosphor material.

17. The method of claim 1, wherein the object is a biological sample.

18. The method of claim 9, wherein each of the first and second objects comprises a biological sample.

19. The method of claim 9, further comprising the step of removing the labels from the first substrate or first and second substrate.

20. The method of claim 19, wherein the label removing step is performed after the steps of attaching the first and second objects and before the processing step.

21. The method of claim 1, wherein the attaching step is performed by printing the object onto the particle label.

22. The method of claim 9, wherein the attaching steps are performed by printing the first and second objects onto their respective first and second particle labels.

23. The method of claim 1, wherein the printing in the printing step comprises ink jet printing.

24. The method of claim 1, wherein the printing in the printing step comprises thermal wax transfer printing.

25. The method of claim 1, wherein the printing in the printing step comprises contact printing.

26. The method of claim 9, wherein the printing in at least one of the printing steps comprises ink jet printing.

27. The method of claim 9, wherein the printing in at least one of the printing steps comprises thermal wax transfer printing.

28. The method of claim 9, wherein the printing in at least one of the printing steps comprises contact printing.

* * * * *

UNITED STATES PATENT AND TRADEMARK OFFICE
CERTIFICATE OF CORRECTION

PATENT NO.        : 8,673,107 B2                                                     Page 1 of 1
APPLICATION NO.   : 12/091900
DATED             : March 18, 2014
INVENTOR(S)       : Robert C. Haushalter It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 277 days.

Signed and Sealed this

Twenty-ninth Day of September, 2015

Michelle K. Lee
*Director of the United States Patent and Trademark Office*